US00RE37741E

(19) United States
(12) Reissued Patent
Zlotnick

(10) Patent Number: US RE37,741 E
(45) Date of Reissued Patent: Jun. 11, 2002

(54) PURIFIED NONTYPABLE HAEMOPHILUS INFLUENZAE P5 PROTEIN AS A VACCINE FOR NONTYPABLE HAEMOPHILUS INFLUENZAE INFECTION

(75) Inventor: Gary W. Zlotnick, Penfield, NY (US)

(73) Assignee: American Cyanamid Company, Madison, NJ (US)

(21) Appl. No.: 09/599,652

(22) Filed: Jun. 21, 2000

Related U.S. Patent Documents

Reissue of:
(64) Patent No.: 5,770,213
Issued: Jun. 23, 1998
Appl. No.: 08/210,394
Filed: May 5, 1994

(51) Int. Cl.[7] ..... A61K 39/102; A61K 39/00; C07K 1/36; C07K 14/285

(52) U.S. Cl. ..... 424/256.1; 424/184.1; 424/185.1; 424/831; 530/350; 530/412; 530/807

(58) Field of Search ..... 424/256.1, 184.1, 424/185.1, 831; 530/300, 350, 324, 326, 412, 807

(56) References Cited

U.S. PATENT DOCUMENTS 5,098,997 A 3/1992 Anilionis et al. ..... 530/350
5,766,608 A 6/1998 Kolattukudy et al. .... 424/256.1

OTHER PUBLICATIONS

Purification and Partial Characterization of Outer Membrane Proteins P5 and P6 from Haemophilus Influenzae Type b. American Society for Microbiology, R. Munson, Jr. and D. Granoff, May 1985.*

Spinola, S. M., et al., The Major Outer Membrane Protein of Haemophilus ducreyi Is a Member of the OmpA Family of Proteins, Infection and Immunity, Apr. 1993, pp. 1346–1351.*

Faden, H., et al., Otitis Media in Children. I. The Systemic Immune Response to Nontypable Haemophilus influenzae, 1989, The Journal of Infectious Diseases, vol. 160, No. 6, pp. 999–1004.*

Munson et al., Infection & Immunity 61:4017–4020, Sep. 1993.

Hughes et al., ABSTRACTS of the 92nd General Meeting of the American Society for Microbiology, p. 106, Abstr. D–63, 1992.

Munson et al., Infection & Immunity 49:544–549, 1985.

Green et al., Infection & Immunity 61:1950–1957, 1993.

Houghten et al., VACCINES, 86 New Approaches to Immunization, pp. 21–25, 1986.

Munson, Jr. et al., ABSTRACTS of the 24th Interscience Conference on Antimicrobial Agents & Chemotherapy, held in Washington, D.C. on Oct. 8–10, 1984, p. 234, Abstr. No. 829.

Spinola et al., Infection & Immunity 61:1346–1351, Apr. 1993.

Faden et al., Journal of Infection Diseases 160(6):999–1004, 1989.

Loeb et al., Infection & Immunity 55:2612–2618, 1987.

L. van Alphen et al., Infection & Immunity 56:1800–1806, 1988.

T. Sirakova et al., Infection & Immunity 62:2002–2020, 1994.

* cited by examiner

*Primary Examiner*—Jennifer E. Graser
(74) *Attorney, Agent, or Firm*—Alan M. Gordon; Anne M. Rosenblum

(57) ABSTRACT

The present invention relates to P5 outer membrane protein of the non-typable *Haemophilus influenzae* bacterial strain and antibodies directed to P5 protein. The invention also relates to a method of isolating P5 protein and a vaccine composition for use in the treatment of non-typable *Haemophilus influenzae* infection.

24 Claims, 6 Drawing Sheets

```
                 APKDNTWYTGAKLGWSQYHDTGFINNNGPTHEN.QLGAG...........
                          10        20        30        40        50
NTHi P5 (P860    APQENTFYAGVKAGQGSFHD.GINNNGAIKEDSIDLTLGYGYRRNTFTYG   49
Ecoli OMP A s    APKDNTWYTGAKLGWSQYHDTGFINNNGPTHEN.QLGAG...........   38
Sd OMP A         APKDNTWYTGAKLGWSQYHDTGFIDNNGPTHEN.QLGAG...........   38

                 AFGGYQVNPYVGF....EMGYDWLGRMPYKG.SVENGAYKAQGVQLTAKL
                          60        70        80        90       100
NTHi P5 (P860    VFGGYQILNQDNFGLAAELGYDNFGRVKFRAEGKTKAKHTNHGAHLSLKG   99
Ecoli OMP A s    AFGGYQVNPYVGF....EMGYDWLGRMPYKG.SVENGAYKAQGVQLTAKL   83
Sd OMP A         AFGGYQVNPYVGF....EMGYDWLGRMPYKG.SVENGAYKAQGVQLTAKL   83

                 GYPITDDLDVYTRLGGMVWRADTK..XXXNXTXXX.XKNHDTGVSPVFAG
                         110       120       130       140       150
NTHi P5 (P860    SYEVLDGLDVYGKAGVALVRSDYKFYEAPNSTRDXKKGTHTARASGLFAV  149
Ecoli OMP A s    GYPITDDLDIYTRLGGMVWRADTK..SNVY......GKNHDTGVSPVFAG  125
Sd OMP A         GYPITDDLDVYTRLGGMVWRADTK..AHNNVTGES.EKNHDTGVSPVFAG  130

                 GVEYAITPEIATRLEYQWTNNIG.......DAHTIGTR.......PDNGX
                         160       170       180       190       200
NTHi PT (P860    GAEYAVLPELAVRLEYQQLTRVGKYRPQDKNAPSIN.PNTAIHYNPXIGS  198
Ecoli OMP A s    GVEYAITPEIATRLEYQWTNNIG.......DAHTIGTR.......PDNGM  161
Sd OMP A         GVEWAITPEIATRLEYQWTNNIG.......DAHTIGTR.......PDNGL  166
```

FIG.2A

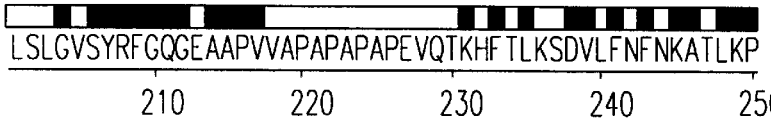

```
NTHi PT (P860   INAGISYRFGQG.AAPV.............KTFSLNLDVTFAFGKANLKP  234
Ecoli OMP A s   LSLGVSYRFGQGEAAPVVAPAPAPAPEVQTKHFTLKSDVLFNFNKATLKP  211
Sd OMP A        LSLGVSYRFGQGEAAPVVAPAPAPAPEVQTKHFTLKSDVLFNFNKATLKP  216
```

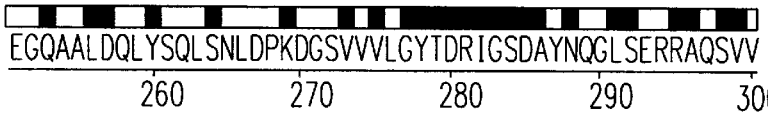

```
NTHi PT (P860   QAQATLDSIYGEMSQV..KSAKVAVAGYTDRIGSDAFNVKLSQERADSVA  282
Ecoli OMP A s   EGQAALDQLYSQLSNLDPKDGSVVVLGYTDRIGSDAYNQGLSERRAQSVV  261
Sd OMP A        EGQAALDQLYSQLSNLDPKDGSVVVLGYTDRIGSDAYNQGLSERRAQSVV  266
```

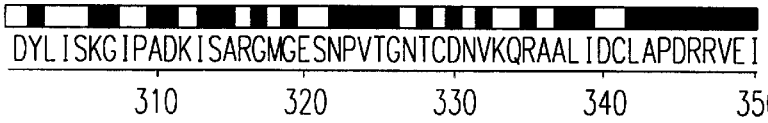

```
NTHi PT (P860   NYFVAKGVAADAISATGYGKANPVTGATXDQVWGRWALIATLAPDRRVEI  332
Ecoli OMP A s   DYLISKGIPADKISARGMGESNPVTGNTCDNVKQRAALIDCLAPDRRVEI  311
Sd OMP A        DYLISKGIPADKISARGMGESNPVTGNTCDNVKQRAALIDCLAPDRRVEI  316
```

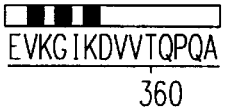

```
NTHi PT (P860   AVNGTK                                              338
Ecoli OMP A s   EVKGIKDVVTQPQA                                      325
Sd OMP A        EVKGIKDVVTQPQA                                      330
```

FIG.2B

| STRAIN | BC ENDPOINT TITER |
|---|---|
| P860295 | 40 |
| P880859 | 10 |
| S2 | 10 |
| P861454 | 40 |
| POSITIVE CONTROL (TOTAL MEMBRANES FROM P860295) | >640 |

FIG.5

PURIFIED NONTYPABLE HAEMOPHILUS INFLUENZAE P5 PROTEIN AS A VACCINE FOR NONTYPABLE HAEMOPHILUS INFLUENZAE INFECTION

Matter enclosed in heavy brackets [ ] appears in the original patent but forms no part of this reissue specification; matter printed in italics indicates the additions made by reissue.

*This is a reissue of U.S. Pat. No. 5,770,213 issued on Jun. 23, 1998 from application Ser. No. 08/210,394 filed on May 5, 1994.*

FIELD OF INVENTION

The present invention relates to P5 outer membrane protein of the Haemophilus influenzae bacterial strain and antibodies directed to P5 protein. The invention also relates to a method of isolating P5 protein and a vaccine composition for use in the treatment of Haemophilus influenzae infection.

BACKGROUND OF INVENTION

Haemophilus influenzae strains are divided into two groups, typable and nontypable. Strains which possess a known capsule are typed by a serological reaction of the capsule with reference antisera. Currently, types a–f have been identified as typable. Strains which do not possess a capsule and fail to react with any of the reference antisera are nontypable.

Nontypable Haemophilus influenzae (NTHI) infections are implicated in several disease states including otitis media, sinusitis, and chronic pulmonary obstructive disease. Haemophilus influenzae type b (Hib) is a major cause of meningitis and other invasive infections in children under the age of four years. Antibodies directed against the capsular polysaccharide of the organism are bactericidal, opsonic in vitro and protective in experimental animals and humans. As used herein, opsonic is defined as preparation of the surface of microorganisms so that they can be more readily taken-up by phagocytes. While safe and effective vaccines for the prevention of Haemophilus influenzae type B disease have been produced, the vaccines are all based on producing antibodies to the polysaccharide capsule which is exterior to the cell wall in the bacteria. NTHi strains of Haemophilus influenzae strains by definition lack a capsule. Therefore, antibodies to capsule will not be effective at preventing NTHi infections.

It is of interest to characterize outer membrane proteins of Haemophilus influenzae bacteria and assess their vaccine potential. Munson et al., (J. Clin. Invest, 72:677–684 (1983)) reported the purification and characterization of P2, one of the major outer membrane proteins of Haemophilus influenzae strains. The researchers found that P2 protein is present in high concentrations, is easily purified, and induces protective antibody in rabbits. P5 protein is thought to be associated with the outer membrane protein layer and was previously extracted by solubilization with sodium dedecyl sulfate (SDS) and organic solvent fractionation. (Coulton et al. Can. J. Microbiology. 20:280–287 (1983)). It has been suggested, however, that the use of SDS may denature proteins in certain circumstances.

Munson and Granoff (American Society of Microbiology (p. 544. (1985)), have reported the partial characterization of P5 and P6 proteins. The results indicated that while P6 cell wall complex elicited antibody in rabbits which had protective activity in the infant rat model, P5 did not yield antiserum which was protective in [infants] *infant* rats nor did [it atisera revert wth] *its antisera react with* surface of bacteria by immunofluorescence which had immunofluorescence activity in vitro. Based on these findings those skilled in the art concluded that P5 was not a vaccine candidate for the prevention of disease caused by Haemophilus influenzae type b.

SUMMARY OF THE INVENTION

It is an object of the present invention, therefore, to provide essentially pure P5 outer membrane protein of Haemophilus influenzae bacteria, antibodies directed to P5 protein and a vaccine composition for use in the treatment of Haemophilus influenzae infective strains.

It is a further object of the present invention to provide a method of purifying P5 protein from the outer membrane of Haemophilus influenzae bacteria and which yields protein which can be used to produce active antibodies. Thus, P5 can be used to produce a vaccine for NTHi and type b strains of Haemophilus influenzae. The invention may be more fully understood by reference to the following drawings and detailed description.

BRIEF DESCRIPTION OF THE DRAWINGS

[FIG. 2: Provides] *FIGS. 2A and 2B: Provide* the amino acid sequence of purified P5 protein (SEQ ID NO:1), which is capable of eliciting a bactericidal antibody. Alignment using Clustal method with PAM250 residue weight table.

FIG. 5: Provides bactericidal activity of mouse P5 antiserum from P860295 against several different non-typable Haemophilus strains. BC endpoint=reciprocal of the highest dilution producing >50% killing. Mice were vaxed (study #T93-0016) at weeks 0, 4, 8, 12 with 10 ug/animal of NTHi P5 from P860295+3DMPL via subcutaneous injection. BC endpoint titers represented here are from week 10 bleeds. Pre sera were screened and did not show any bactericidal activity.

DETAILED DESCRIPTION OF THE PREFERRED EMBODIMENT

Figure 1:
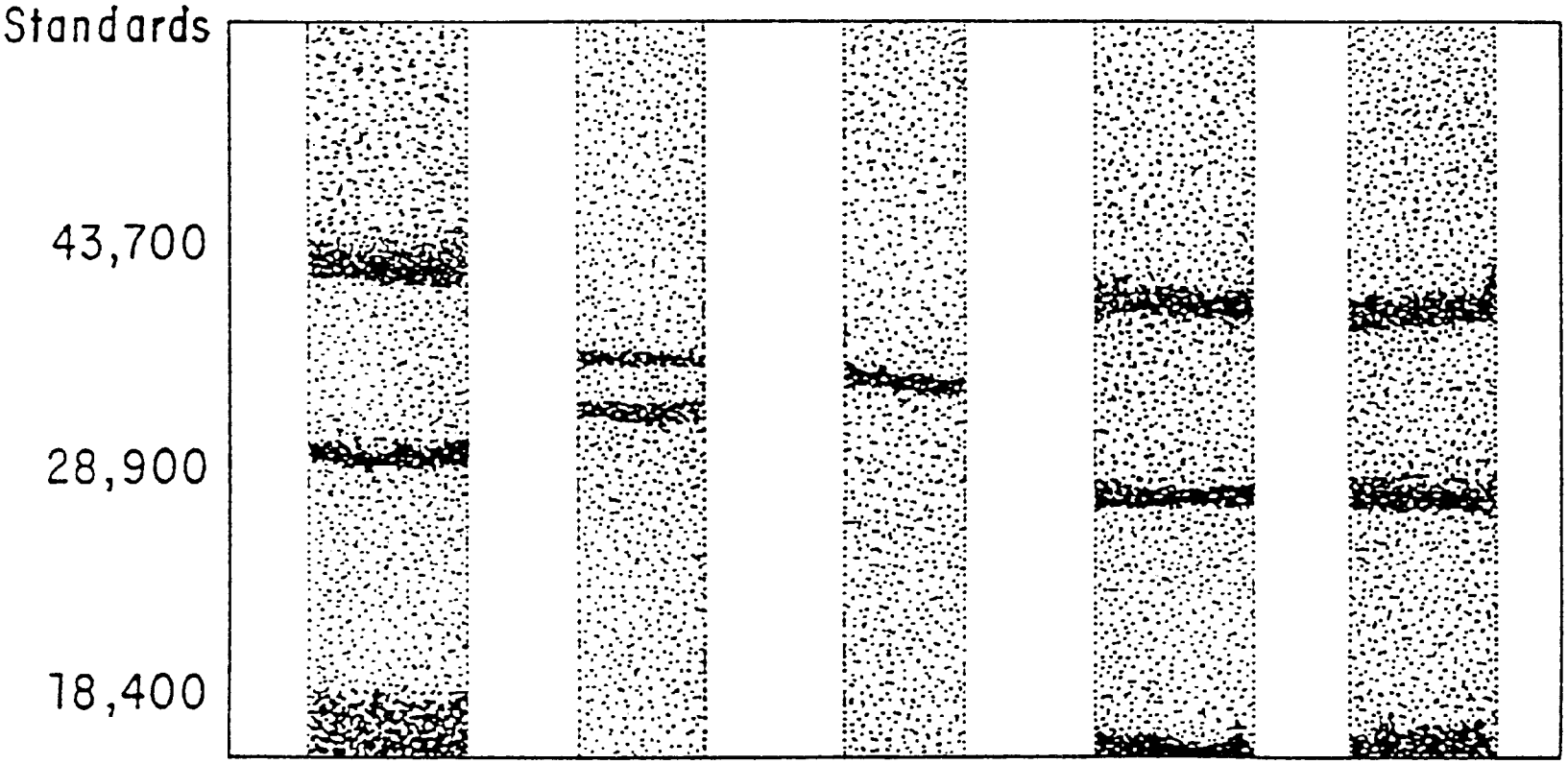
FIG. 1: Provides a sodium dodecyl sulfate (SDS) gel of purified non-typable and type B P5 proteins. Lane 1 depicts nontypable P5 (P860295); lane 2 depicts type B P5 (Eagan). The doublet in lane 1 represents the heat modified and non-heat modified forms of P5 protein. P5 from NTHi strain P860295 (lane 1) and from HIB Eagan (lane 2) were analyzed in 15% SDS-PAGE gels. The doublet in lane 1 represents the heat modified and non heat modified forms of P5.

The present invention relates to a purified P5 outer membrane protein of non-typable Haemophilus influenzae bacteria. The P5 protein is a 28–35 KDa heat modifiable outer membrane protein with both conserved and variable regions.

P5 protein has several properties that make it (and peptides and proteins having epitopes of P5 protein) especially valuable for vaccination against non-typable Haemophilus influenzae. As used herein, epitope is defined as a region of an antigen to which the variable region of an antibody binds. Most antigens have a large number of epitopes, and therefore a polyvalant antiserum to the antigen will contain a large number of different antibodies, each antibody capable of binding to a different epitope on the antigen. In contrast to reports published in the prior art, P5 protein is capable of eliciting antibodies that react to the bacteria's surface and are bactericidal. The protein has been purified by and has been shown to induce an immune response against different strains of non-typable Haemophilus influenzea.

The peptides or proteins of the present invention bear a common epitope with P5 protein and thus are immunologically crossreactive therewith. They can include fragments or oligopeptides containing epitopes of P5 protein. As used herein, oligopeptides are defined as polymeric chains of a few monomeric repeat units. The amino acid sequence of P5 protein has been determined and is shown in [FIG. 2] *FIGS. 2A and 2B* (SEQ ID NO:1). The peptides and proteins of the present invention comprise any peptide or protein having at least a portion of the amino acid sequence depicted in [FIG. 2] *FIGS. 2A and 2B* (SEQ ID NO:1) or any biologically equivalent sequences. Altered sequences include sequences in which functionally equivalent amino acid residues are substituted for residues within the sequence resulting in a silent change. For example, one or more amino acid residues within the sequence can be substituted for another amino add of a similar polarity which acts as a functional equivalent, resulting in a silent alteration. Substitutes for an amino acid within the sequence may be selected from other members of the class to which the amino acid belongs. For example, the nonpolar (hydrophobic) amino acids include glycine, alanine, leucine, isoleucine, valine, proline, phenylalanine, tryptophan and methionine. The polar neutral amino acids include serine, threonine, cysteine, tyrosine, asparagine, and glutamine. The charged (basic) amino acids include arginine, lysine and histidine. The negatively charged (acidic) amino acids include aspartic and glutamic acid.

The peptides and proteins of the present invention also include fragments or oligopeptides having epitopes of P5 protein represented within the sequence or any analogues of such fragments or epitopes. In addition, any of the peptides and proteins can be modified for conjugation to other molecules, e.g. by the attachment of coupling groups such as the amino acids cysteine and lysine or other linking groups.

As described in detail below. P5 protein and the peptides and proteins of this invention are useful in many different forms. (e.g. alone or in mixtures) in vaccines. For these purposes, the peptides and proteins are produced by isolation from Haemophilus influenzae or by chemical synthesis, or potentially by biotechnology methods such as recombinant expression in various host cells.

Native P5 protein is purified from Haemophilus influenzae by a procedure of differential detergent extraction. The procedure does not involve the use of denaturants and reducing agents such as sodium dodecylsulfate and 2-mercaptoethanol, respectively, which can destroy important antigenic epitopes of the protein and which are not widely accepted as safe for administration to humans.

The procedure entails first obtaining outer membrane components of Haemophilus influenzae cells. Outer membrane components can be prepared from a total cell membrane fraction. Total membrane fractions are typically prepared by differential sedimentation after disruption of Haemophilus influenzae cells by methods such as sonication, grinding, or expulsion from a french press or other homogenization device. The total membrane fraction is then fractionated into inner and outer membranes by density gradient sedimentation or by differential solubilization of the inner membrane constituents with certain detergents such as polyoxyethyleneoctylphenol (Triton X-100™) or N-lauroyl sarcosine, sodium salt (sarcosyl). In the preferred embodiment, outer cell membrane components are prepared by differential solubilization of inner membranes in 0.1–2%(w/v) Triton X-100 in 100 mM HEPES-NaOH 1 mM $MgCl_2$, pH 7.4. This extraction is typically performed twice.

As an alternate source of outer membrane components, a culture medium of Haemophilus influenzea cells is useful. The medium contains shed components (called "blebs") of the outer membrane of the bacteria. See Loeb., M. R. (1987) Infection and Immunity 55 (11):2612–2618.

Solubilization of P5 protein from the outer membrane-cell wall complex is then achieved by a three-step differential solubilization. In the first step, an aqueous solution of 0.1–10%, typically 0.1–2% (w.v) dodecylsulfobetaine (Zwittergent™ 3-14) is used to remove outer membrane proteins. Preferably, a 1% solution is used and the extraction is usually performed 2–3 times. Following Zwittergent™ 3-14 and 0.5M NaCl extractions the P5 protein is solubilized with 1% sarcosyl in 50 mM Tris-HCl, pH8, 5 mM $Na_2EDTA$. The extracts are adjusted to 1% Zwittergent™ 3-14 in the same buffer and dialyzed against 10 fold excess of 1% Zwittergent™ 3-14 in 50 mM Tris-HCl, pH8, 5 mM $Na_2EDTA$ (3×) over 24 hours. The dialyzed extract is then passed through an anion exchange (DEAE) column and a cation exchange (S) column connected in tandem. The columns are separated and the S column is eluted with an increasing salt gradient in the same Zwittergent containing buffer, the purified P5 protein is eluted as a single peak as analyzed by SDS-PAGE (FIG. 1).

P5 protein purified by this method is substantially free of bacterial endotoxin and is suitable for administration to humanbeings. The purified preparation of P5 protein is then formulated alone as a pharmaceutical composition, as for example a vaccine for Haemophilus influenzae, or in a mixture with adjuvants and/or with antigens of other organisms implicated in otitis media of other diseases. If desired, the protein is fragmented by standard chemical or enzymatic techniques to produce antigenic segments.

The peptides and proteins of this invention can be chemically synthesized according to the amino acid sequence shown in [FIG. 2] *FIGS. 2A and 2B* (SEQ ID NO:1) or variations of this sequence as described above. Any of the standard chemistries for solid or liquid phase synthesis of peptides and proteins are useful. Chemical synthesis may be particularly suitable for production of oligopeptides containing epitopes of P5 protein.

Experience with antibodies to the capsular polysaccharide of Haemophilus influenzae shows that the ability of the antibodies to kill the bacteria in in vitro assays is closely correlated with the ability to elicit a protective immune response in human infants (Fedea et al., J. Infect. Dis., 160, 999–1004 (1989)).

Anti-P5 protein antibodies elicited in response to the peptides and proteins of this invention are tested using similar in vitro assay systems to demonstrate the ability to kill Haemophilus influenzae cells. These results show a similar correlation with the potential of the P5 protein to elicit a protective immune response and to serve in a vaccine for human infants, children and adults.

An in vitro complement mediated bactericidal assay system (Musher et al., 1983, Infect. Immun. 39:297–304; Anderson et al., 1972, *J. Clin, Invest.* 51:31–38) which has been used previously for measuring bactericidal activity of antibodies to PRP and lipopolysaccharide (LPS) against Haemophilus influenzae is useful to determine whether antibody directed against a particular peptide protein or fragment thereof has bactericidal activity against nontypable Haemophilus influenzae.

The peptides and proteins of the present invention are useful as immunogens in subunit vaccines for vaccination against nontypable Haemophilus influenzae. The vaccines are useful to prevent or reduce susceptibility to acute otitis media and other diseases caused by nontypable strains of the organism, generally to vaccinate children or adults against otitis media or to children at risk of contracting otitis media or other diseases (for example, children with a history of ear infection).

The peptides and proteins of this invention are formulated as univalent and multivalent vaccines. As used herein univalent vaccines are defined as single component and multivalent vaccines are defined as multi-component.

P5 protein itself is used as produced or isolated by the methods described above or mixed, with other antigens.

The peptides or proteins of this invention are administered as multivalent subunit vaccines in combination with other antigens of Haemophilus influenzae.

As mentioned, peptides and proteins having epitopes of P5 protein evoke bactericidal antibodies which act synergistically in killing Haemophilus influenzae with antibodies against other outer membrane proteins of Haemophilus influenzae. Thus, in an embodiment of the invention, P5 protein (or a peptide or protein having a common epitope) is administered in conjunction with other outer membrane proteins of Haemophilus influenzae (or peptides or proteins having epitopes thereof) to achieve a synergistic bactericidal activity. Particularly preferred outer membrane proteins of Haemophilus influenzae are the peptidoglycan-associated outer membrane lipoprotein (PAL) and the Haemophilus lipoprotein PAL cross-reacting protein (PCP) described by Deich. P. A. et al. (1988) *J. Bacteriol.* 170(2): 489–498, the teachings of which are incorporated by reference herein. For combined administration with epitopes of other outer membrane proteins, the P5 protein *or* peptide is either administered separately, as a mixture or as a conjugate or genetic fusion peptide or protein. For example, the PAL and PCP or any proteins, peptides or epitopes derived from them, is administered as a mixture or as a conjugate or fusion with a P5 protein or a P5 protein derived peptide or protein. The conjugates is formed by standard techniques for coupling proteinaceous materials. P5 protein or any derived peptides or proteins can be used in conjunction with antigens of other organisms (e.g. encapsulated or nonencapsulated, bacteria, viruses, fungi and parasites). For example, P5 protein is useful in conjunction with antigens of other microorganisms implicated in otitis media or other diseases. These included Streptococcus pneumonia, Streptococcus pyogenes, group A, Staphylococus aureus, respiratory syncytial virus and Branhemella catarrhalis.

In formulating the vaccine compositions with the peptide or protein, alone or in the various combinations described, the immunogen is adjusted to an appropriate concentration and formulated with any suitable vaccine adjuvant. The immunogen may also be incorporated into liposomes, or conjugated to polysaccharides and/or other polymers for use in a vaccine formulation.

Vaccines of the present invention are administered to humanbeings or animals in a variety of ways. These include intradermal, intramuscular, intraperitoneal, intravenous, subcutaneous, oral and intranasal routes of administration.

The peptide and proteins of this invention is also administered as a live vaccine. To this end, recombinant microorganisms are prepared that express the peptides or proteins. The vaccine recipient is inoculated with the recombinant microorganism which multiplies in the recipient, expresses the P5 protein peptide or protein and evokes a immune response of Haemophilus influenzae. Preferred live vaccine vectors are pox viruses such as vaccinia (Paoletti and Panicali. U.S. Pat. No. 4,603,112) and attenuated Salmonella strains (Stocker, U.S. Pat. No. 4,550.081).

Live vaccines are particularly advantageous because they lead to a prolonged stimulus which can confer substantially long-lasting immunity. When the immune response is protective against subsequent Haemophilus influenzae infection, the live vaccine itself may be used in a preventative vaccine against Haemophilus influenzae.

Multivalent five vaccines are prepared from a single or a few recombinant microorganisms which express different epitopes of Haemophilus influenzae (e.g., other outer membrane proteins such as PAL and PCP or epitopes thereof). In addition, epitopes of other pathogenic microorganisms can be incorporated into the vaccine. For example, a vaccinia virus can be engineered to contain coding sequences for other epitopes in addition to those of Haemophilus influenzae. Such a recombinant virus itself can be used as the immunogen in a multivalent vaccine. Alternatively, a mixture of vaccinia or other viruses, each expressing a different gene encoding for different epitopes of outer membrane proteins of Haemophilus influenzae and/or epitopes of other disease causing organisms can be formulated as a multivalent vaccine.

Another vaccine of the present invention is an inactivated virus vaccine. Inactivated vaccines are "dead" in the sense that their infectivity has been destroyed, usually by chemical treatment (e.g., formaldehyde treatment). Ideally, the infectivity of the virus is destroyed without affecting the proteins which carry the immunogenicity of the virus. In order to prepare inactivated vaccines, large quantities of the recombinant virus expressing the desired epitopes are grown in culture to provide the necessary quantity of relevant antigens. A mixture of inactivated viruses expressing different epitopes is useful for the formulation of "multivalent" vaccines. In certain instances, these "multivalent" inactivated vaccines are preferable to live vaccine formulation because of potential difficulties arising from mutual interference of live viruses administered together. In either case, the inactivated virus or mixture of viruses is formulated in a suitable adjuvant in order to enhance the immunological response to the antigens. Suitable adjuvants include: surface active substances, e.g., hexadecylamine, octadecyl amino acid esters, octadecylamine, lysolecithin, dimethyldioctadecylammonium bromide, N, N-dicoctadecyl-N'-N'bis (2-hydroxyethyl-propane diamine), methoxyhexadecylglycerol, and pluronic polyols; polyamines, e.g., pyran, dextransulfate, poly IC, carbopol; peptides, e.g., muramyl dipeptide, dimethylglycine, tuftsin; oil emulsions; and mineral gels, e.g., aluminum hydroxide, aluminum phosphate, etc.

The peptides and proteins of the present invention also are useful to produce polyclonal antibodies for use in passive immunotherapy against Haemophilus influenzae. Human immunoglobulin is preferred because heterologous immunoglobulun may provoke a deleterious immune response to its foreign immunogenic components. Polycolonal antisera is obtained from individuals immunized with the peptides or proteins in any of the forms described. Immunoglobulin fraction is then enriched. For example, immunoglobulins specific for epitopes of P5 protein are enriched by immunoaffinity techniques employing the peptides or proteins of this invention. The antibody is specifically absorbed from antisera onto an immunoadsorbent containing epitopes of P5 protein and then eluted from the immunoadsorbent as an enriched fraction of immunoglobulin.

In addition, nucleic acids having the nucleotide sequence of the gene encoding P5 protein or any nucleotide sequences which hybridize therewith can be used as probes in nucleic acid hybridization assays for the detection of Haemophilus influenzae in various tissues or body fluids of patients. The probes may be used in any nucleic [any] *acid* type of hybridization assay including: Southern blots (Southern. 1975. J. Mol. Biol. 98:508); Northern blots (Thomas et al., 1989 Proc. Nat'l Acad. Sci. USA 77:5201–05); colony blots (Grunstein et al., 1975, *Proc. Nat'l Acad. Sci. USA* 72:3961–65), etc. Stringency of hybridization can be varied depending on the requirements of the assay.

The invention is further illustrated by the following examples.

EXAMPLE 1

Purification of P5

Protein extracts of P5 are obtained from both NTHi and Hib strains by differential detergent extraction of outer membranes. Following Zwittergent octylglucoside 3-14 and Zwittergent 3-14 and 0.5M NaCl extractions the P5 protein is solubilized with 1% sarcosyl in 50 mM Tris-HCl, pH8, 5 mM $Na_2EDTA$. The extracts are adjusted to 1% Zwittergent™ 3-14 in the same buffer and dialyzed against 10 fold excess of 1% Zwittergent™ 3-14 in 50 mM Tris-HCl, pH8, 5 mM $Na_2EDTA$ (3×) over 24 hours. The dialyzed extract is then passed through an anion exchange (DEAE) column and a cation exchange (S) column connected in tandem. The columns are separated and the S column is eluted with an increasing salt gradient in the same Zwittergent containing buffer. The purified P5 protein is eluted as a single peak as analyzed by SDS-PAGE (FIG. 1).

EXAMPLE 2

Protease Digestion, Peptide Isolation, and Protein Sequencing

Purified NTHi P5 and Hib P5 are used directly to determine the amino acid sequence [(FIG. 2)] (*FIGS. 2A and 2B*) (SEQ ID NO:1). Total sequence of the NTHi Protein (SEQ ID NO:1) is determined by obtaining overlapping peptides by protease digestion with several proteases including endopeptidases Lys-C. Arg-C, Glu-C, papain, trypsin, and chymotrypsin. Cyanogen bromide also is used to cleave the protein, at methionine residues to create large fragments. The peptides are isolated using a microbore High Performance Liquid Chromatograph (HPLC) and the sequences determined with a protein seqencor. Alignment of the peptides utilizes overlapping peptides and homology to the *E. coli* OmpA protein [(FIG. 2)] (*FIGS. 2A and 2B*).

EXAMPLE 3

Whole Cell Elisa Assay

Figure 3:
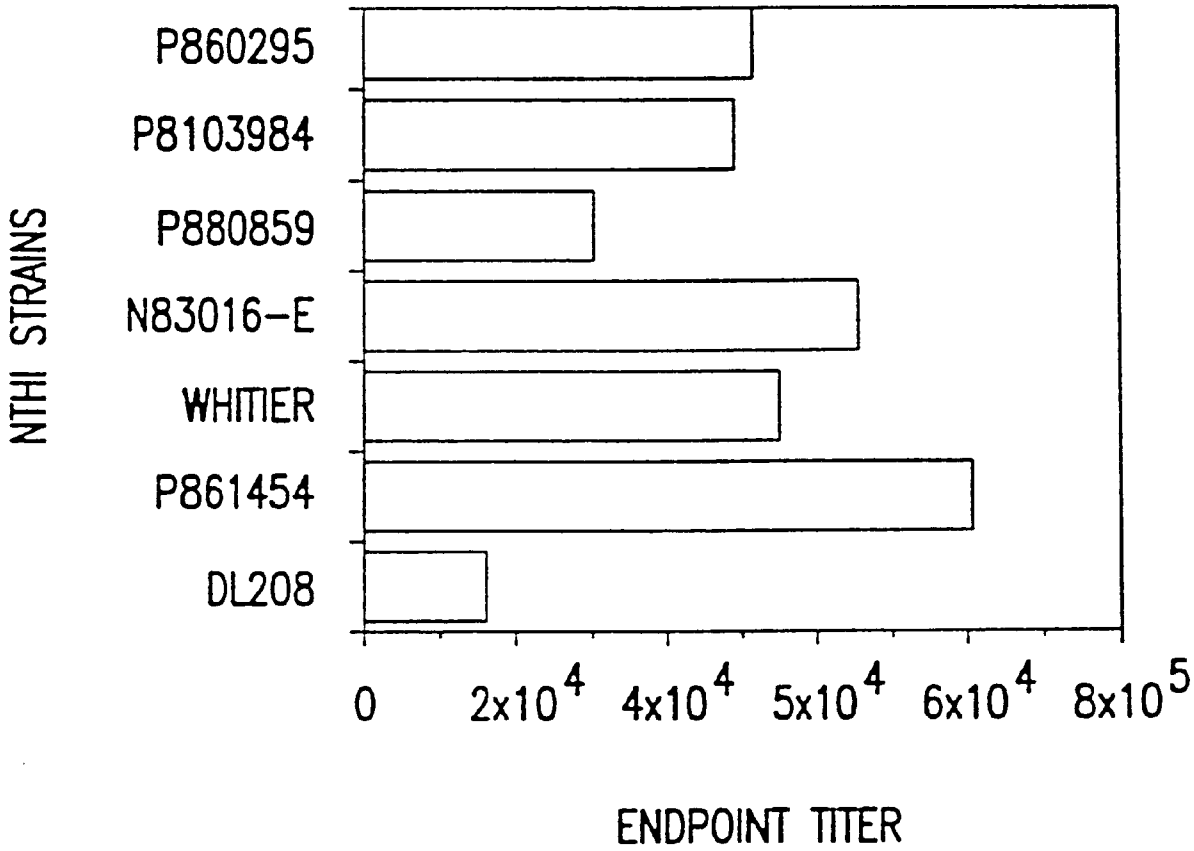
FIG. 3: Provides whole cell Elisa endpoint titers generated from rabbit -antisera directed against NTHi P5. Endpoint titer=the reciprocal of the highest dilution giving an optical density of 0.1 at 405 nm. Rabbits were vaxed (study #T91-3984) at weeks 0, 4, 8 with 15 ug/animal of NTHi P5 from P860295+3DMPL via subcutaneous injection. Endpoint titers represented here are from week 10 bleeds. All pre sera endpoints titered out no greater than 4000. Rabbit antibodies were detected with TAGO goat, anti rabbit IgG+ IgM conjugated to alkaline phosphatase.
Figure 4:
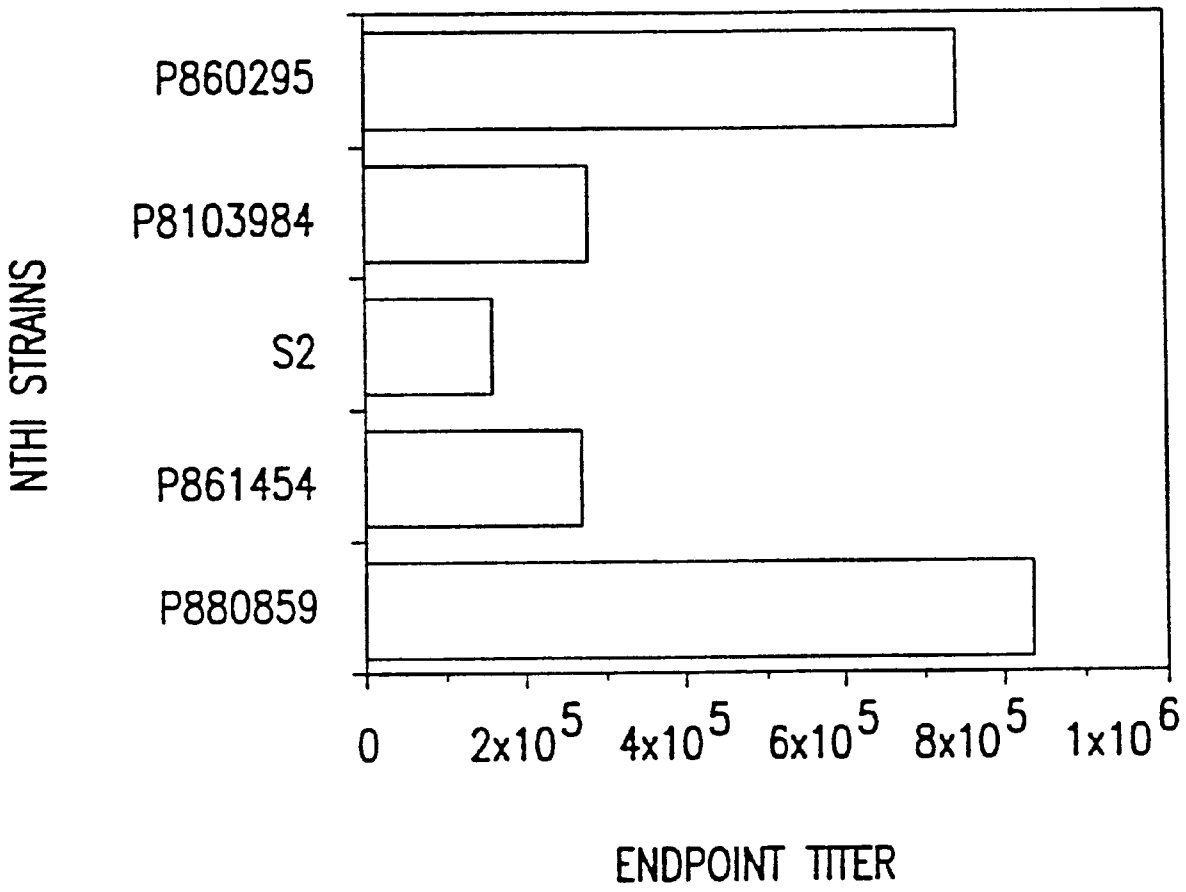
FIG. 4: Provides whole cell Elisa endpoint titers generated from mouse antisera directed against NTHi P5. Endpoint titer=the reciprocal of the highest dilution giving an optical density of 0.1 at 405 nm. Mice were vaxed ((study #T93-0016) at weeks 0, 4, 8, 12 with 10 ug/animal of NTHi P5 from P860295+3DMPL via subcutaneous injection. Endpoint titers represented here are from week 10 bleeds. All pre sera endpoints titered out no greater than 1350. Mouse antibodies were detected with TAGO goat, anti mouse IgG+IgM conjugated to alkaline phosphatase.

Whole formalin fixed Haemophilus Influenzae cells from several different strains are prepared from mid-log phase cells grown to $OD_{490}$=1.0 in BHI-XV media. Cells are washed twice in Phosphate Buffered Saline (PBS) (7 mM NaHPO4-7H20, 2 mM KH2PO4, 2 mM CK1, 137 mM NaCl pH7.4) then resuspended in PBS with 0.3% formalin and incubated at room temperature for 1–2 hours. Formalin is removed by washing cells in PBS and resuspending cells in PBS to a final concentration $OD_{620}$=0.2. Seventy-five microliters of cells are then added to the wells of microtiter plates and dried overnight at 37° C. Plates are blocked with PBS-0.1% Tween-20 for one hour and washed in a microplate washer. One Hundred microliters of antiserum diluted in phosphate buffered saline containing 0.15 mM $CaCl_2$, 0.5 mM $MgCl_2$, 1% gelatin and 0.3% Tween-20 (PCM-GT) are added to the wells and plates are incubated at 37° C. for two hours. After washing, bound antibodies were detected with goat anti-mouse (IgG+IgM) conjugated to alkaline phosphatase (TAGO) diluted in PBS 0.05% Tween-20, 0.1% gelatin for one hour at 37° C. Cells are again washed and plates were developed with a 1 mg/ml solution of p-nitrophenyl phosphate (SIGMA) in diethanolamine for thirty minutes. The reaction is quenched following the addition of 3N NaOH. The plates are read on a reader at $OD_{450}$, reference $OD_{620}$. Whole cell ELISA data for rabbit and mouse anti-P5 serum are shown in FIGS. 3 and 4 respectively.

EXAMPLE 4

Bactericidal Assay

Cells from several different Haemophilus influenzae strains are grown overnight in BHI-XV media. The following day fresh cultures are prepared from a 1:10 dilution of overnight stock and grown to OD490=1.0. During cell growth, a complement source, pre-colostral calf serum is preadsorbed with P860295 cells for one hour. Cells are then pelleted away from complement and preadsorbed complement is sterile filtered though a 0.2 um filter unit and stored on ice prior to use. All antiserum screened in this assay is heat inactivated at 56° C. for fifteen minutes to remove complement activity and diluted 1:5 in PCM followed by subsequent two fold dilutions which are prepared in a sterile 96 well microtiter plates. The bacterial cells grown to an OD410=1.0 are diluted 1:100.000 in PCM containing the complement source at a dilution of 1:5. Fifteen microliters of this mixture is added to the serial dilutions of antiserum and plates were allowed to incubate for forty-five minutes at 37° C. Following this, ten microliters of each reaction are plated on BHI-XV. After overnight incubation at 37° C., colonies are counted to determine bactericidal titers (the reciprocal of the highest dilution of antiserum capable of killing greater than 50% of bacteria as compared to preimmune sera controls). The bactericidal data with respect to P5 is represented in FIG. 5.

SEQUENCE LISTING (1) GENERAL INFORMATION:

(iii) NUMBER OF SEQUENCES: 1

(2) INFORMATION FOR SEQ ID NO:1:

(i) SEQUENCE CHARACTERISTICS:
(A) LENGTH: 338 amino acids
(B) TYPE: amino acid
(C) STRANDEDNESS: unknown
(D) TOPOLOGY: unknown (ii) MOLECULE TYPE: protein (xi) SEQUENCE DESCRIPTION: SEQ ID NO:1:

```
Ala Pro Gln Glu Asn Thr Phe Tyr Ala Gly V al Lys Ala Gly Gln Gly
1               5                   10                  15

Ser Phe His Asp Gly Ile Asn Asn Asn Gly A la Ile Lys Glu Asp Ser
            20                  25                  30

Ile Asp Leu Thr Leu Gly Tyr Gly Tyr Arg A rg Asn Thr Phe Thr Tyr
        35                  40                  45

Gly Val Phe Gly Gly Tyr Gln Ile Leu Asn G ln Asp Asn Phe Gly Leu
    50                  55                  60

Ala Ala Glu Leu Gly Tyr Asp Asn Phe Gly A rg Val Lys Phe Arg Ala
65                  70                  75                  80

Glu Gly Lys Thr Lys Ala Lys His Thr Asn H is Gly Ala His Leu Ser
                85                  90                  95

Leu Lys Gly Ser Tyr Glu Val Leu Asp Gly L eu Asp Val Tyr Gly Lys
            100                 105                 110

Ala Gly Val Ala Leu Val Arg Ser Asp Tyr L ys Phe Tyr Glu Ala Pro
        115                 120                 125

Asn Ser Thr Arg Asp Xaa Lys Lys Gly Thr H is Thr Ala Arg Ala Ser
    130                 135                 140

Gly Leu Phe Ala Val Gly Ala Glu Tyr Ala V al Leu Pro Glu Leu Ala
145                 150                 155                 160

Val Arg Leu Glu Tyr Gln Gln Leu Thr Arg V al Gly Lys Tyr Arg Pro
                165                 170                 175

Gln Asp Lys Asn Ala Pro Ser Ile Asn Pro A sn Thr Ala Ile His Tyr
            180                 185                 190

Asn Pro Xaa Ile Gly Ser Ile Asn Ala Gly I le Ser Tyr Arg Phe Gly
        195                 200                 205

Gln Gly Ala Ala Pro Val Lys Thr Phe Ser L eu Asn Leu Asp Val Thr
    210                 215                 220

Phe Ala Phe Gly Lys Ala Asn Leu Lys Pro G ln Ala Gln Ala Thr Leu
225                 230                 235                 240

Asp Ser Ile Tyr Gly Glu Met Ser Gln Val L ys Ser Ala Lys Val Ala
                245                 250                 255

Val Ala Gly Tyr Thr Asp Arg Ile Gly Ser A sp Ala Phe Asn Val Lys
            260                 265                 270

Leu Ser Gln Glu Arg Ala Asp Ser Val Ala A sn Tyr Phe Val Ala Lys
        275                 280                 285

Gly Val Ala Ala Asp Ala Ile Ser Ala Thr G ly Tyr Gly Lys Ala Asn
    290                 295                 300

Pro Val Thr Gly Ala Thr Xaa Asp Gln Val T rp Gly Arg Trp Ala Leu
305                 310                 315                 320
```

-continued

```
Ile Ala Thr Leu Ala Pro Asp Arg Arg Val G lu Ile Ala Val Asn Gly
                325                 330                 335

Thr Lys
```

What is claimed is:

1. P5 outer membrane protein of nontypable Haemophilus influenzae bacterial strains which is substantially free of bacterial endotoxin, which is purified without the use of denaturing detergents or reducing agents and which elicits bactericidal antibodies.

2. The P5 protein of claim 1 wherein the amino acid sequence is provided in [FIG. 2 (SEQ ID NO:1)] *SEQ ID NO:1*, wherein the P5 protein elicits bactericidal antibodies against nontypable Haemophilus influenzae in a host.

3. A preparation of P5 protein of nontypable Haemophilus influenzae which is substantially free of bacterial endotoxin, wherein the protein is purified without the use of denaturing detergents or reducing agents and wherein the protein elicits bactericidal antibodies against nontypable Haemophilus influenzae in a host.

4. A vaccine composition for use in the treatment of nontypable Haemophilus influenzae infections which comprises an effective amount of nontypable Haemophilis influenzae P5 protein which is substantially free of bacterial endotoxin, which is purified without the use of denaturing detergents or reducing agents and which elicits bactericidal antibodies against nontypable Haemophilus influenzae in a host; in a pharmaceutically acceptable vehicle, and an optional adjuvant.

5. The vaccine composition of claim 4, further comprising at least one additional antigen or one or more organisms.

6. The vaccine composition of claim 5, wherein the organism is selected from the group consisting of a bacterium, virus, parasite and fungus.

7. The vaccine composition of claim 5, wherein the organism or organisms are etiologic agents of otitis media, or sinusitis or chronic pulmonary obstructive disease.

8. The vaccine composition of claim 5, wherein the organism or organisms are etiologic agents of meningitis.

9. The vaccine composition of claim 8, wherein the organism is selected [frog] *from* the group consisting of: Streptococcus pneumonia, Streptococcus pyogenes, Group A, Staphylococcus aureus, Branhamella catarrhalis, and respiratory syncytial virus.

10. The vaccine composition of claim 5, wherein the additional antigen is an outer membrane protein of nontypable Haemophilus influenzae.

11. The vaccine composition of claim 10, wherein the outer membrane protein is selected from the group consisting of peptidoglycan-associated outer membrane lipoprotein [Haemophilus lipoprotein, PAL or] *of Haemophilus* (*PAL*) *and* PAL cross-reacting protein (PCP).

12. A vaccine composition comprising an antigen conjugate comprising nontypable Haemophilus influenzae P5 protein which is substantially free of bacterial endotoxin, which is purified without the use of denaturing detergents or reducing agents and which elicits bactericidal antibodies against nontypable Haemophilus influenzae in a host, conjugated to an antigen of an organism or an epitope or epitopes of that antigen, in a pharmaceutically acceptable vehicle.

13. The vaccine composition of claim 12, wherein the organism is nontypable Haemophilus influenzae.

14. The vaccine composition of claim 13 wherein the antigen is an [oligo] *oligo-* or polysaccharide antigen of nontypable Haemophilus influenzae.

15. The vaccine composition of claim 12, wherein the antigen is an outer membrane protein of nontypable Haemophilus influenzae.

16. [A] *The* vaccine composition of claim 15 wherein the outer membrane protein is peptidoglycan-associated outer membrane lipoprotein [Haemophilus lipoprotein] *of Haemophilus*.

17. A method of treating against nontypable Haemophilus influenzae, comprising administering to an individual an immunogenic amount of P5 protein of nontypable Haemophilus influenzae which is substantially free of bacterial endotoxin, wherein said P5 protein is purified without the use of denaturing detergents or reducing agents and which elicits bactericidal antibodies against nontypable Haemophilus influenzae in a host.

18. [A] *The* method of claim 17 wherein P5 protein has the amino acid sequence shown in [FIG. 2 (SEQ ID NO:1)] *SEQ ID NO:1*.

19. The method of claim 18 wherein the P5 protein is administered in conjunction with at least one other antigen of nontypable Haemophilus influenzae.

20. The method of claim 19, wherein the antigen is an oligo- or polysaccharide or an outer membrane protein of nontypable Haemophilus influenzae.

21. The method of claim 20, wherein the outer membrane protein is peptidoglycan-associated outer membrane lipoprotein [Haemophilus lipoprotein] *of Haemophilus*.

22. A method of reducing susceptibility to acute otitis media, sinusitis or chronic pulmonary obstructive disease comprising administering to an individual an immunogenic amount of P5 protein of nontypable Haemophilus influenzae which is substantially free of bacterial endotoxin, wherein said P5 protein [in] *is* purified without the use of denaturing detergents or reducing agents and which elicits bactericidal antibodies against nontypable Haemophilus influenzae in a host.

23. The vaccine composition of claim 12 which further comprises an adjuvant.

24. The preparation of claim 3 which further comprises an adjuvant.

* * * * *